United States Patent [19]

Kirchhof

[11] 4,334,018

[45] Jun. 8, 1982

[54] PROCESS AND REAGENT FOR THE DETERMINATION OF PROTHROMBIN

[75] Inventor: Bruno Kirchhof, Münster, Fed. Rep. of Germany

[73] Assignee: Boehringer Mannheim GmbH, Mannheim, Fed. Rep. of Germany

[21] Appl. No.: 216,696

[22] Filed: Dec. 15, 1980

Related U.S. Application Data

[63] Continuation of Ser. No. 971,600, Dec. 20, 1978, abandoned.

[30] Foreign Application Priority Data

Dec. 24, 1977 [DE] Fed. Rep. of Germany ....... 2757992

[51] Int. Cl.³ .......................... C12Q 1/38; C12Q 1/56
[52] U.S. Cl. ......................................... 435/13; 435/23
[58] Field of Search .................... 435/13, 23, 212, 214

[56] References Cited

U.S. PATENT DOCUMENTS

| | | | |
|---|---|---|---|
| 3,486,981 | 12/1969 | Speck | 435/13 |
| 3,884,896 | 5/1975 | Blomback et al. | 435/13 X |
| 4,061,625 | 12/1977 | Ekenstam et al. | 435/13 X |
| 4,070,245 | 1/1978 | Svendsen | 435/13 |
| 4,139,415 | 2/1979 | Yin et al. | 435/13 |

OTHER PUBLICATIONS

Thaubaut et al., Chemical Abstracts, 85:188, 186x (1976), p. 180.
Whitaker, *Principles of Enzymology for the Food Sciences,* Marcel Dekker, Inc., New York, (1972), 364.
Bergstroem et al., Chemical Abstracts, 81:101546k (1974), p. 218.
Witt, Chemical Abstracts, 87:179596v (1977), p. 211.
Esnouf et al., *Biochem. J., 131, (1973), 781-789.*
Yue et al., Biochim. Biophys. Acta, 490 (1977), 350-362.
Vermeer et al., Thrombosis Research, 10 (1977), 495-507.
Berse et al., Biochem. J., 135 (1973) 791-795.
Radcliffe et al., J. Biol. Chem., 247(23), (1972), 7735-7742.
Rosenberg et al., J. Biol. Chem., 250(5), (1975), 1607-1617.

*Primary Examiner*—Esther M. Kepplinger
*Attorney, Agent, or Firm*—Felfe & Lynch

[57] ABSTRACT

A novel process for the determination of prothrombin in biological material, by conversion of prothrombin into thrombin, enzymatic fission of a thrombin substrate and measurement of a fission product, the improvement comprising incubating the test solution with the addition of Factor Xa.

25 Claims, No Drawings

PROCESS AND REAGENT FOR THE DETERMINATION OF PROTHROMBIN

This is a continuation of application Ser. No. 971,600, filed Dec. 20, 1978, abandoned.

The present invention is concerned with a process and a reagent for the determination of prothrombin in biological material, such as blood plasma.

The determination of the prothrombin level is an important clinical parameter for the continuous monitoring of anticoagulation therapy. Equally important is the detection of a Factor-II deficiency which can not only be inherited but can also be acquired, i.e. as a result of a primary fundamental disease.

Starting from natural thrombin-substrate fibrinogen, in the course of the development of prothrombin determination methods, use is now made of synthetic chromogenic substrates, for example peptide-p-nitroanilide derivatives, tissue thromboplastin being used as activator. One disadvantage of this method is, for example, the fact that the optimum activation time varies with the prothrombin concentration. Furthermore, there is a lack of specificity. In the case of other substrates, it would be necessary to have lower plasma concentrations in the activation mixture in order to determine prothrombin in normal plasma. However, due to such a high plasma dilution, it was not possible to achieve a complete activation in plasmas with low prothrombin activity. Staphylocoagulase and snake venoms have also been used as activators. They activated prothrombin directly. However, it has been found that these venoms at least partly also activated the PIVKA-prothrombin which is formed during treatment with oral anticoagulants. Staphylocoagulase also reacts with this so-called PIVKA-prothrombin.

Therefore, there has been a need for a method and reagent for the determination of prothrobin in plasma which permits the carrying out of such a test with few sources of error, increased precision and sensitivity and improved reproduceability. Such a test is to be specific, i.e., only to detect prothrombin but not also PIVKA-prothrombin. All the prothrombin is thereby to be converted quickly and completely into thrombin without the activator necessary for this purpose thereby participating in any way in the color reaction.

The present invention provides such a method and reagent. Essentially, in the present invention, prothrombin in biological material, for example in blood plasma, is determined by conversion of prothrombin into thrombin, enzymatic fission of thrombin substrate and measurement of a fission product, wherein the test solution is incubated with the addition of Factor Xa.

Although human Factor Xa has proved to be the best, it is also possible to use, for example, bovine Factor Xa.

The principle of this method of determination can be explained as follows: from, for example, oligopeptides in which p-nitroaniline is attached, as chromogenic group, on to the carboxyl group of arginine by amide formation, thrombin splits off p-nitroaniline:

N—Tos—Gly—Pro—Arg—pNA $\xrightarrow[\text{H}_2\text{O}]{\text{thrombin}}$

N—Tos—Gly—Pro—Arg—OH + pNA

Examples of thrombin substrates which have proved to be especially useful include N-Tos-Gly-Pro-Arg-pNA and N-Cbz-Gly-Pro-Arg-pNA (Chromozyme TH; Boehringer Mannheim GmbH), as well as H-D-Phe-Pip-Arg-pNA (S-2238) and Bz-Phe-Val-Arg-pNA (S-2160). The yellow color of the free p-nitroanilines can be measured photometrically at about 390 to 410 nm, the amount of colored material liberated per unit time being proportional to the enzyme activity.

As buffer for carrying out the method, it is preferred to use tris and/or imidazole buffer with a pH of about 8 to 9, to which hydrochloric acid and/or sodium chloride can be added.

Phospholipids and calcium chloride can be added as co-reagents for the activation of the prothrombin.

The addition of the substrate takes place after complete conversion of the prothrombin into thrombin in the test solution, after the addition of Factor Xa.

The Factor Xa used according to the present invention is readily obtainable by a simple process which is also the subject matter of the present invention. According to this process, plasma and preferably human plasma is treated with a prothrombin activator, centrifuged, mixed with a protein adsorbent, the precipitate obtained eluted with a protein elution agent and the eluate mixed with a Factor X activator and possibly with a soluble calcium salt. The prothrombin activator used is advantageously *Echis carinatus* venom but there can also be used other snake venoms, such as Taipan snake venom (*Oxyuranus scutellatus*) and trypsin.

The coagulate obtained after treatment with the prothrombin activator, which is centrifuged off, consists partly of fibrinogen, antithrombin and thrombin.

The protein adsorbent used is preferably barium sulphate, citrate or oxalate but there can also be used, for example, aluminium hydroxide, DEAE-Sephadex and QAE-Sephadex.

The protein elution agent used can be, for example, an aqueous solution of trisodium citrate, a phosphate buffer or an aqueous solution of sodium chloride.

Russell's viper venom is particularly preferred as the Factor X activator.

As soluble calcium salt, it is preferred to use calcium chloride.

If the eluate, after treatment with the protein elution agent, contains components which have a negative effect on the coagulation system, for example calcium-binding components, such as citrate ions when the protein elution agent is sodium citrate, it is necessary to introduce a dialysis step. In the case mentioned, for example, dialysis is carried out against a buffered physiological solution of sodium chloride (Michaelis buffer) at a low temperature, i.e. at about 4° C.

After the treatment with the Factor X activator and the addition of the calcium ion-containing solution, the preparation is, before use, left to stand at a low temperature and preferably at about 4° C. for the complete conversion of Factor X into Factor Xa. Further steps can subsequently be carried out in order to obtain highly purified Factor Xa. These further purification steps can comprise gel filtration with a molecular sieve which differentiates the range of from 50,000 to 100,000, for example "Sephadex" G 100 or "Biogel" P 100, eluting with, for example, sodium actate buffer (0.4 molar; pH 7). Furthermore, it is also possible to carry out an ammonium sulphate precipitation (for example with a 45 to 55% solution; pH 6 to 8), an ion exchange chromatography with DEAE-"Sephadex" A 50, DEAE-cellulose or QAE-"Sephadex"/cellulose, using as buffer sodium potassium phosphate (for example 0.02 molar; pH 6.8) or a gradient of 0.1 to 1.0 molar aqueous sodium chloride solution. It is also possible to carry out a treatment with hydroxyapatite (phosphate buffer 0.2 to 0.5 molar; pH 6.8), as well as preparative electrophoresis and possibly ultracentrifuging. The above-mentioned methods are advantageously combined. Factor Xa purified in this manner can be used in the test in the form of a solution, for example in veronal or Michaelis buffer, in physiological sodium chloride solution or in the test buffer. However, for use in the test according to the present invention, this purification procedure can be omitted and the Factor Xa preparation, enriched in the above-described manner, used.

The present invention also provides a reagent for the determination of prothrombin, comprising a thrombin substrate and a prothrombin activator, the prothrombin activator being Factor Xa and preferably human Factor Xa.

This reagent preferably consists essentially of tris- and/or imidazole buffer and human Factor Xa as prothrombin activator. As co-reagents, it is advantageous to use phospholipids from human brain and calcium chloride, as well as a synthetic thrombin substrate. Such a reagent preferably comprises:
0.3 to 6.5 μg./ml. phospholipids,
0.7 to 10 mM/liter calcium chloride and
150 to 380 μM/liter substrate,
the Factor Xa concentration corresponding to 0.2 to 2.5% of the plasma extract. The reagent can be in dried or dissolved form.

The process and reagent according to the present invention permit a rapid and dependable determination of prothrombin. The process is characterized by its specificity because Factor Xa only detects normal prothrombin but not also PIVKA-prothrombin. The previously employed activators certainly did not act specifically. The addition of a standardized Factor Xa preparation ensures that, in every case, a sufficient amount of activator is present. It was very surprising that Factor Xa, after the addition thereof, converted all of the prothrombin rapidly and completely into thrombin without itself participating in any way in the color reaction, which is of great importance. Thus, it is known that the Factor Xa has a direct splitting action on, for example, synthetic peptide-p-nitroaniline derivatives, such as Chromozyme TH. In particular, it was also surprising that human Factor Xa can be used more advantageously than, for example, bovine Factor Xa. It has proved to be especially advantageous to add Factor Xa in definite amounts; the activation of Factor Xa itself present in blood plasma would here give rise to unsatisfactory results. Furthermore, it was surprising that, by means of such a simple preparative process, such as that according to the present invention, an activator can be made available which ensures practicability and especially technical usefulness and, having regard to its origin, namely human plasma, could be sufficiently produced at all.

The following Examples are given for the purpose of illustrating the present invention:

EXAMPLE 1

Production of a Factor Xa preparation

Normal plasma is obtained from the blood of healthy donors with an average age of 30 years, half of the donors being male and half being female. It contains 25 mM sodium citrate. After a first centrifuging for 15 minutes at 1500 g and at ambient temperature, the plasma is subjected to a second centrifuging at 4° C. for 30 minutes at 20,000 g. Per 4 ml. normal plasma, there are added 1 ml. 1/30 molar aqueous calcium chloride solution and 2 drops of *Echis carinatus* venom (Sigma V 8250; fundamental solutions in each case 1 mg./ml. water) and left to stand for about 2 hours in a waterbath at 37° C. The resulting coagulate is centrifuged off and 150 mg. barium sulphate added to the supernatant obtained from each 4 ml. of normal plasma. The mixture is stirred for 30 minutes at ambient temperature and then centrifuged. The supernatant is discarded and the precipitate washed four times with approximately 4 ml. amounts of physiological sodium chloride solution. The centrifugate is eluted with 2 ml. of a 0.2 molar trisodium citrate solution (pH 7.0). After again centrifuging, the supernatant is dialysed against physiological sodium chloride solution at 4° C. The dialysate is stored in small amounts of about 250 μl. at −20° C. To each portion are added, at ambient temperature, 30 μl. of a 0.1 molar calcium chloride solution and 1 μl. Russell's viper venom (*Vipera russelli*, Wellcome) and the mixture left to stand for about 14 hours at 4° C. This preparation can be used in the test, 2 μl. corresponding to 1% plasma extract. It can also be lyophilized. Further purification can also be carried out in the manner described in detail hereinbefore.

EXAMPLE 2

Method for the determination of prothrombin and thrombin

Test mixtures were prepared which contained the following components:

| substance | volume | final concentration |
|---|---|---|
| buffer solution | 400 μl., minus the other amounts added | |
| test plasma | 1 to 5 μl. | |
| phospholipids | 2 μl. | 0.25 to 1.25% |
| calcium chloride solution | 40 μl. (0.1 m) | 1.25 μg./ml. |
| activator (Factor Xa preparation according to Example 1) | 2 μl. | 10 mM/l. corresponding to 1% plasma fraction |

The buffer solution is prepared as follows:
stock solution A: 0.1 M/l. tris+0.1 M/l. imidazole+0.1 M/l. hydrochloric acid
stock solution B: 0.1 M/l. tris+0.1 M/l. imidazole+0.1 M/l. sodium chloride
stock solution C: 0.2 M/l. sodium chloride.

The buffer used (pH 8.4) is prepared by combining the stock solutions in the volume ratio A:B:C of 1:1:2. The phospholipids used were an acetone/diethyl ether extract of human brain obtained by Bell and Alton's method.

The components of the test mixture are pipetted directly in the given order into a microcuvette with a layer thickness of 1 cm. of an "Aminco DW 2" spectrophotometer at 37° C. The incubation time for Factor Xa is 120 seconds. There are then added thereto 50 μl. (1.5 mM/l.) substrate (Chromozyme TH; Boehringer Mannheim GmbH or Substrate 2238, Kabi), the end concentration thereby being 187.5 μM/l. for Chromozyme TH and 148 μM/l. for Substrate 2238. After thoroughly mixing as quickly as possible, commencement of measurement begins immediately.

The absorption per unit time is recorded directly with an indicator rate in minutes per cm. in the horizontal and an absorption in mm. per mm. full scale in the vertical. Various absorption sensitivities and running speeds can hereby be selected. Therefore, the change of absorption per minute can be calculated according to the following formula:

$$\frac{\frac{\text{measured absorption in mm.}}{\text{total scale in mm.}} \times \text{absorption sensitivity}}{\text{indicator rate in min./cm.} \times \text{measurements stretch}}$$

Example for measurement stretch 10 cm., vertical 43 mm., full scale 252 mm., absorption sensitivity 0.5 and running speed 0.033:

$$\frac{\frac{43}{252} \times 0.5}{0.033 \times 10 \text{ min./cm}} = 0.258 \frac{\text{absorption change}}{\text{minute}}$$

It will be understood that the specification and examples are illustrative, but not limitative, of the present invention and that other embodiments within the spirit and scope of the invention will suggest themselves to those skilled in the art.

What is claimed is:

1. In a process for the determination of prothrombin in biological material, by conversion of prothrombin into thrombin, enzymatic fission of a thrombin substrate and measurement of product, the improvement comprising incubating the test solution with the addition of Factor Xa as the sole enzyme activating prothrombin into thrombin.

2. Process as claimed in claim 1, wherein human Factor Xa is added.

3. Process as claimed in claim 1, wherein the Factor Xa is produced by treating plasma with a prothrombin activator, centrifuging, mixing the supernatant with a protein adsorbent, eluting the precipitate with a protein elution agent and mixing the eluate with a Factor X activator and optionally with a soluble calcium salt.

4. Process as claimed in claim 3, wherein human plasma is used.

5. Process as claimed in claim 1 wherein the thrombin substrate is a synthetic peptide-p-nitroanilide derivative.

6. Process as claimed in claim 5, wherein the thrombin substrate is N-Tos-Gly-Pro-Arg-pNA, N-Cbz-Gly-Pro-Arg-pNA, H-D-Phe-Pip-Arg-pNA or Bz-Phe-Val-Arg-pNA.

7. Process as claimed in claim 1, wherein the biological material is blood plasma.

8. Reagent for the determination of prothrombin in biological material, comprising a thrombin substrate and a prothrombin activator, wherein the prothrombin activator is Factor Xa in a concentration of from 0.2 to 2.5% of the biological material.

9. Reactant as claimed in claim 8 wherein the prothrombin activator is human Factor Xa.

10. Reagent as claimed in claim 8 wherein the Factor Xa is prepared by treating plasma with a prothrombin activator, centrifuging, mixing the supernatant with a protein adsorbent, eluting the precipitate with a protein elution agent and mixing the eluate with a Factor X activator and optionally with a soluble calcium salt.

11. Reagent as claimed in claim 10 wherein human plasma is used as the biological material.

12. Reagent for the determination of prothrombin in biological material, comprising a buffer selected from the group consisting of tris and imidazole buffers, Factor Xa, co-reagents for Factor Xa and a synthetic thrombin substrate said Factor Xa being in a concentration of from 0.2 to 2.5% of the biological material.

13. Reagent as claimed in claim 12 wherein human Factor Xa is used.

14. Reagent as claimed in claim 12 wherein the Factor Xa is prepared by treating plasma with a prothrombin activator, centrifuging, mixing the supernatant with a protein adsorbent, eluting the precipitate with a protein elution agent and mixing the eluate with a Factor X activator and optionally with a soluble calcium salt.

15. Reagent as claimed in claim 14 wherein human plasma is used.

16. Reagent as claimed in claim 12 wherein the coreagents are phospholipids and calcium chloride.

17. Reagent as claimed in claim 12 wherein the synthetic thrombin substrate is N-Tos-Gly-Pro-Arg-pNA, H-D-Phe-Pip-Arg-pNA, N-Cbz-Gly-Pro-Arg-pNA or Bz-Phe-Val-Arg-pNA.

18. Reagent as claimed in claim 16 comprising 0.3 to 6.5 g./ml. of phospholipids, 0.7 to 10 mM/liter calcium chloride and 150 to 380 M/liter thrombin substrate, the Factor Xa concentration corresponding to 0.2 to 2.5% of the plasma extract.

19. In a process for the determination of prothrombin in biological material, by conversion of prothrombin into thrombin, enzymatic fission of a thrombin substrate and measurement of product, the improvement comprising incubating the test solution with Factor Xa in a concentration of from 0.2 to 2.5% of the biological material extract.

20. Improvement as claimed in claim 19 wherein human Factor Xa is added.

21. Improvement as claimed in claim 19 wherein Factor Xa is produced by treating plasma with a prothrombin activator, centrifuging, mixing the supernatant with a protein adsorbent, eluting the precipitate with a protein elution agent and mixing the eluate with Factor X activator and optionally with a soluble calcium salt.

22. Improvement as claimed in claim 21 wherein human plasma is used.

23. Improvement as claimed in claim 19 wherein the thrombin substrate is a synthetic peptide-nitroanilide derivative.

24. Improvement as claimed in claim 19 wherein the thrombin substrate is N-Tos-Gly-Pro-Arg-pNA, N-Cbz-Gly-Pro-Arg-pNA, H-D-Phe-Pip-Arg-pNA, or Bz-Phe-Val-Arg-pNA.

25. Improvement as claimed in claim 19 wherein the biological material is blood plasma.

* * * * *